(12) United States Patent
Davidson et al.

(10) Patent No.: US 8,448,534 B2
(45) Date of Patent: May 28, 2013

(54) METHOD AND APPARATUS FOR DISPERSING A SAMPLE OF PARTICULATE MATERIAL

(75) Inventors: Nicholas Craig Davidson, St. Johns (GB); Margaret Ellen Dyson, Droitwich (GB); Jonathan Powell, Ross-on-Wye (GB); Andrew John Prior, Malvern (GB)

(73) Assignee: Malvern Instruments Incorporated, Southborough, MA (US)

( * ) Notice: Subject to any disclaimer, the term of this patent is extended or adjusted under 35 U.S.C. 154(b) by 198 days.

(21) Appl. No.: 12/451,563

(22) PCT Filed: May 19, 2008

(86) PCT No.: PCT/GB2008/001702
§ 371 (c)(1),
(2), (4) Date: Sep. 7, 2010

(87) PCT Pub. No.: WO2008/142387
PCT Pub. Date: Nov. 27, 2008

(65) Prior Publication Data
US 2010/0326213 A1 Dec. 30, 2010

(30) Foreign Application Priority Data
May 18, 2007 (GB) .................................. 0709639.9

(51) Int. Cl.
*G01N 15/00* (2006.01)
(52) U.S. Cl.
USPC ....................................................... 73/865.5
(58) Field of Classification Search
None
See application file for complete search history.

(56) References Cited

U.S. PATENT DOCUMENTS

| 2,977,787 | A | 4/1961 | Holcomb |
| 3,461,268 | A | 8/1969 | Inoue |
| 3,472,202 | A | 10/1969 | Todd |
| 3,552,653 | A | 1/1971 | Inoue |
| 3,584,798 | A | 6/1971 | Metreveli |

(Continued)

FOREIGN PATENT DOCUMENTS

| DE | 2461377 A1 | 7/1975 |
| DE | 68917293 T2 | 4/1995 |

(Continued)

OTHER PUBLICATIONS

Ankersmid International, PD-10: Unique Dry Powder Disperser for Highly Uniform Slide Preparation, 1991.
Ankersmid Ltd., New Product Announcement—Eyetech Microscopy—Dry Powder Dispersion and Automated Image Analysis for Microscopy, 1991.

(Continued)

*Primary Examiner* — Robert R Raevis
(74) *Attorney, Agent, or Firm* — Kristofer E. Elbing

(57) ABSTRACT

An apparatus for dispersing a sample of particulate material, includes a carrier (31;35;37;38;39) having a sample-bearing surface on which to place the sample, and a housing (10;44; 48) for forming a dispersion chamber (17), at least when closed off at a base (46;51). The carrier is arranged such that the sample-bearing surface is removed from contact with the sample upon application of a sufficient pressure differential across the carrier between the sample-bearing surface and an opposite side of the carrier. The housing (10;44;48) has an inlet (26) at least partially facing the base (46;51). The apparatus includes an apparatus (15;16) for passing a volume of fluid past the carrier (31;35;37;38;39) through the inlet (26) by subjecting the carrier (31;35;37;38;39) to a pulsed positive pressure differential relative to the dispersion chamber (17).

32 Claims, 16 Drawing Sheets

U.S. PATENT DOCUMENTS

| | | | |
|---|---|---|---|
| 3,644,984 | A | 2/1972 | Inoue |
| 4,017,007 | A | 4/1977 | Riccio |
| 4,067,291 | A | 1/1978 | Park |
| 4,469,722 | A | 9/1984 | Danielson |
| 4,726,936 | A | 2/1988 | Erdt |
| 4,868,128 | A | 9/1989 | Sommer |
| 5,038,866 | A | 8/1991 | Kern |
| 5,215,221 | A | 6/1993 | Dirksing |
| 5,239,358 | A | 8/1993 | Tokoyama |
| 5,240,606 | A | 8/1993 | Lapidus |
| 5,296,910 | A * | 3/1994 | Cole ........................... 356/28.5 |
| 5,305,957 | A | 4/1994 | Szocs |
| 5,522,555 | A | 6/1996 | Poole |
| 5,790,308 | A | 8/1998 | Kamentsky |
| 5,875,776 | A | 3/1999 | Vaghefi |
| 6,047,644 | A | 4/2000 | Malecki |
| 6,209,538 | B1 | 4/2001 | Casper |
| 6,722,364 | B2 | 4/2004 | Connelly |
| 7,041,153 | B2 | 5/2006 | Totoki |
| 7,455,248 | B2 * | 11/2008 | Kablik et al. ................. 239/654 |
| 7,883,902 | B2 | 2/2011 | Chapeau |
| 2002/0127701 | A1 | 9/2002 | Duncan |
| 2002/0197631 | A1 | 12/2002 | Lawrence |
| 2003/0047184 | A1 * | 3/2003 | Lockhart et al. ......... 128/203.21 |
| 2003/0155452 | A1 * | 8/2003 | Herget ........................ 239/650 |
| 2003/0190366 | A1 | 10/2003 | Maa |
| 2004/0151360 | A1 | 8/2004 | Pirard |
| 2005/0005717 | A1 * | 1/2005 | Pensis et al. ................. 73/866.5 |
| 2008/0261325 | A1 | 10/2008 | Chapeau |

FOREIGN PATENT DOCUMENTS

| | | |
|---|---|---|
| EP | 1754040 | 2/2007 |
| FR | 2696831 | 4/1994 |
| GB | 2384190 | 7/2003 |
| JP | 46022412UM | 8/1971 |
| JP | 46022413UM | 8/1971 |
| JP | 62242836 | 10/1987 |
| JP | 63181854 | 11/1988 |
| JP | 2001095918 A2 | 4/2001 |
| JP | 2001242062 | 9/2001 |
| JP | 2003337086 | 11/2003 |
| JP | 2004010917 A2 | 1/2004 |
| SU | 1065033 | 1/1984 |
| WO | WO8707024 | 11/1987 |
| WO | WO9424263 | 10/1994 |
| WO | WO9612513 | 5/1996 |
| WO | WO9620022 | 7/1996 |
| WO | WO9701365 | 1/1997 |
| WO | WO9711732 | 4/1997 |
| WO | WO0105455 | 1/2001 |
| WO | WO0211894 A1 | 2/2002 |
| WO | WO0230500 | 4/2002 |
| WO | WO0230501 | 4/2002 |
| WO | WO03074154 | 9/2003 |
| WO | WO2005124311 | 12/2005 |

OTHER PUBLICATIONS

Barreiros et al., Calculating Shape Factors from Particle Sizing Data, Particle & Particle Systems Characterization, VCH Verlagsgesellschaft mbH, D-69469 Weinheim, 1996, 368-373, vol. 13, Iss. 6.

Cheng et al., Powder Aspirator for Shock Tube Studies of Heterogeneous Reactions, The Review of Scientific Instruments, Feb. 1988, 322-327, vol. 59, Iss. 2.

Cohen et al., Chemical Mechanism for Secondary Flash Suppression, Eighteenth Symposium (International) on Combustion, 1981, 225-231.

Decker et al., Shock Tube Powder Dispersal Unit, Review of Scientific Instruments, Mar. 1987, 476-478, vol. 58, Iss. 3.

Decker et al., US Statutory Inventions Register, Registration No. H146, Oct. 7, 1986.

Ferraris et al., Measurement of Particle Size Distribution in Portland Cement Powder, Cement, Concrete and Aggregates, vol. 26, No. 2, Dec. 2004.

Gregoire et al., Accuracy of Size Distributions Obtained from Single Particle Static Digital Image Analysis, PARTEC 2007.

Harnby, The Sampling of Particulate Mixtures, POWERTEC '75—Proceedings of the Third International Powder Technology and Bulk Solids Conference, Powder Technology Publication Series No. 6, 1976, Heyden, London, New York, Rheine.

Hawkins et al., Sampling Powders for Shape Description, European Symposium on Particle Characterization, May 1984.

Hooker et al., Shock Tube Studies on Two-Phase Systems: Oscillator Strengths of Molecular Band Systems, Physica, 1969, 35-46, vol. 41.

Horiba, Sales Brochure, Jun. 1997.

Kendall, The Delivery of Particulate Vaccines and Drugs to Human Skin with a Practical, Hand-Held Shock Tube-Based System, Shock Waves, 2002, 23-30, vol. 12.

Kuhn et al., Infrared-Optical Transmission and Reflection Measurements on Loose Powders, Review of Scientific Instruments, American Institute of Physics, Sep. 1993, 2523-2530, vol. 64, No. 9.

Moneghini et al., Study of the Solid State of Carbamazepine After Processing with Gas Anti-Solvent Technique, European Journal of Pharmaceutics and Biopharmaceutics 56 (2003), 281-289.

Pirard et al., Direct Estimation of Sieve Size Distributions from 2-D Image Analysis of Sand Particles, PARTEC 2004.

Rajathurai et al., A Shock and Expansion Wave-driven Powder Disperser, Aerosol Science and Technology, 1990, 12:613-619, vol. 12, Iss. 3, Elsevier Science Publishing Co., Inc.

Sanford et al., An Improved, Helium-Driven Biolistic Device, Technique-A Journal of Methods in Cell and Molecular Biology—Feb. 1991, 3-16, vol. 3, No. 1.

Spicer et al., Dry Powder Precursors of Cubic Liquid Crystalline Nanoparticles (Cubosomes*), Journal of Nanoparticle Research, May 2002, 297-311, vol. 4.

Watson et al., Techniques for Conducting Shock Tube Experiments with Mixtures of Ultrafine Solid Particles and Gases, The Review of Scientific Instruments, Aug. 1967, 1052-1057, vol. 38, Iss. 8.

* cited by examiner

METHOD AND APPARATUS FOR DISPERSING A SAMPLE OF PARTICULATE MATERIAL

This application is a U.S. national phase application under 35 USC§371, and claims priority to PCT patent application number PCT/GB2008/001702 having an International filing date of May 19, 2008, which, in turn, claims priority to United Kingdom patent application number GB 0706939.9 having a filing date of May 18, 2007, both of which are herewith incorporated by reference.

The invention relates to an apparatus for dispersing a sample of particulate material, including:
- a carrier having a sample-bearing surface on which to place the sample,
- the carrier being arranged such that the sample-bearing surface is removed from contact with the sample upon application of a sufficient pressure differential across the carrier between the sample-bearing surface and an opposite side of the carrier, and
- a housing for forming a dispersion chamber, at least when closed off at a base, the housing having an inlet at least partially facing the base.

The invention also relates to an assembly for particle analysis, including an apparatus for analysis of particles deposited on a sample collection surface and an apparatus for dispersing a sample of particulate material.

The invention also relates to a method of dispersing a sample of particulate material, the method including:
- providing the sample on a sample-bearing surface of a carrier, the carrier being arranged such that the sample-bearing surface is removed from contact with the sample upon application of a sufficient pressure differential across the carrier between the sample-bearing surface and an opposite surface of the carrier, and
- providing a sample collection surface in a dispersion chamber, wherein the carrier with the sample is provided in the path of flow of fluid conducted, in use, by a fluid duct leading to the dispersion chamber.

The invention also relates to a membrane for use in an apparatus for dispersing a sample of particulate material.

The invention also relates to a set of membranes for use in an apparatus for dispersing a sample of particulate material.

The invention also relates to a sample carrier for use in an apparatus for dispersing a sample of particulate material.

The invention also relates to a kit of parts for use in an apparatus for dispersing a sample of particulate material.

The invention also relates to a set of replaceable modules for use in an apparatus for dispersing a sample of particulate material.

An example of such an apparatus and method is known. WO 2005/124311 discloses a method and device for dispersion of a sample of dry powder in a dispersion chamber. A specific embodiment of the device comprises a vacuum pump, a manometer, means for introduction of a sample in the dispersion chamber, in the shape of a membrane for supporting the sample, on which a sample of dry powder is intended to be placed, and a surface on which the dry powder is to be dispersed. To realise the dispersion operation, an explosion of low intensity is generated. This explosion is produced by the rupture of the sample-carrying membrane, the membrane being inserted between a surrounding environment and the dispersion chamber in which an at least partial vacuum has previously been established. The sample of dry powder is collected for analysis purposes by a process of natural sedimentation of the grains in the dispersion chamber on the surface to be treated.

A problem of the known method and device is that it easily leads to the particles being broken up and interacting with the walls of the dispersion chamber, e.g. by shattering and/or by acquiring static charge. Break-up of particles is a problem when the particles are to be dispersed for the purpose of analysing the particle sizes. Charged particles tend to chain together, and to stand up from the substrate onto which they are dispersed. This makes an analysis of their original sizes more difficult.

It is an object of the invention to provide an apparatus and method of the types defined in the opening paragraphs that are suitable for effecting a relatively controlled dispersion of particulate material, resulting in a relatively homogeneous dispersion of the particles.

This object is achieved by the apparatus according to the invention, which is characterised in that the apparatus includes an apparatus for passing a volume of fluid past the carrier through the inlet by subjecting the carrier to a pulsed positive pressure differential relative to the dispersion chamber.

A pulsed positive pressure differential has a temporal profile showing at least a falling flank. The apparatus for passing a volume of fluid past the carrier need not be energised, but may be, for instance a cylinder of pressurised fluid. By passing a volume of fluid past the carrier such that the carrier is subjected to the pulsed positive pressure differential, the particulate material is dispersed, but dispersion energy is confined to a limited time interval. The particles are accelerated and then allowed to decelerate before hitting the surface on which they are collected. The short burst of acceleration reduces the likelihood of interaction with walls of the dispersion chamber, so that there is also a lower likelihood that the particles will shatter on a surface or acquire electric charge. The dispersion of particles is more homogeneous, because the pressure pulse is easier to control. It is in particular controllable independently of the geometry of the duct and dispersion chamber which would determine the pressure profile of a dispersion chamber under vacuum when explosively returned to ambient pressure.

An embodiment of the apparatus includes a system for controlling the volume of fluid passed past the carrier.

An effect is that the characteristics of the dispersing shear flow that is established upon removal of the sample-bearing surface from contact with the sample can be influenced through the value of the volume of fluid.

An embodiment of the apparatus includes a system for subjecting the carrier to a pressure pulse with at least one of a pre-determined pressure profile and a pre-determined peak value in the inlet.

In an example, the pre-determined pressure profile is a ramp with a pre-determined gradient.

In particular where the pre-determined gradient is low, an effect is to be able to create a stable closed loop control of the volume of air passed into the dispersion chamber. When the carrier gives way upon being subjected to the pressure pulse, this can be detected and the fluid flow arrested before an unnecessary large volume of the fluid is forced through the inlet. A relatively slow measurement system for detecting the removal of the sample-bearing surface from contact with the sample can be employed.

In an embodiment, the carrier includes a membrane, arranged to rupture upon application of a sufficient pressure differential across the membrane.

An effect is to allow the sample on the sample-bearing surface to be placed centrally in the flow of fluid. An added effect associated with a rupturing membrane is that is a relatively easy means of arranging that generally the entire sample-bearing surface is removed from contact with the sample. This makes for a more homogeneous dispersion of the sample.

In an embodiment, the membrane is weakened according to a pattern, symmetric with respect to a normal to the sample-bearing surface.

Controlled weakening can be achieved through careful design of the structural form of the membrane. The symmetric pattern ensures that there is no preferential direction of dispersion of the particulate material, resulting in a relatively homogeneous dispersion of the sample.

In an embodiment, the membrane is weakened along a plurality of line segments extending in respective essentially radial direction with respect to a normal to the sample-bearing surface.

An effect is that membrane parts are prevented from detaching upon rupture. Another effect is that the dispersion is generally co-axial with respect to a centre-line normal to the sample-bearing surface. This can be desirable to reduce the likelihood of particles impacting on sidewalls of the dispersion chamber.

In an embodiment, the membrane is weakened along at least three radially extending line segments and, to a lesser extent than along the radially extending line segments, along at least one line segment connecting points removed from radially innermost end points on angularly neighbouring ones of the radially extending line segments.

An effect is to define surface portions of the membrane that fold away when the membrane is ruptured. The radially extending line segments function as tear lines. The connecting line segments function as hinges over which the surface portions fold away. The repeatability of sample preparation is increased, because the flow pattern established for each membrane is generally the same if the pressure pulse shape and fluid volume are also the same.

An embodiment of the apparatus includes a fitting for receiving a module supporting the membrane in the path of flow of fluid conducted, in use, by a duct in fluid connection with the inlet, wherein the fitting includes a mechanism for engaging the module such as to hold the module in a pre-determined orientation.

An effect is that the sample to be dispersed is dispersed from an intended, repeatable position.

In an embodiment, the carrier is removably arranged in the apparatus.

An effect is that the sample to be dispersed can be prepared away from the apparatus. This reduces the chance of spillage and contamination.

In an embodiment, at least the sample-bearing surface is electrically conducting, and the sample-bearing surface is electrically connected to earth.

An effect is that the electric charge on the particles prior to the moment of dispersal is minimised. Very little electric charge is acquired during dispersal. The dispersed sample is thus relatively free from charged particles. These are undesired, because they make subsequent optical analysis of the dispersed particles difficult. Charged particles tend to chain together in a way that makes it difficult for analytical methods to distinguish between particles. Moreover, elongate charged particles tend to "stand on end" on a substrate when dispersed onto that substrate. They thus present reduced dimensions to analytical apparatus with which they are observed.

In an embodiment, the apparatus for passing a volume of fluid past the carrier through the inlet is arranged to subject the carrier to a pulsed positive pressure differential relative to an ambient air pressure.

A variant subjecting the carrier to a pulsed positive pressure differential relative to ambient air pressure makes the dispersion operation easier to prepare, since a vacuum need not first be established in the dispersion chamber. Dispersion of particles into a dispersion chamber which is not at a (technical) vacuum, i.e. is already filled with fluid, will ensure that the particles are adequately decelerated before impacting on surfaces, reducing the likelihood of particle break-up. Moreover, the volume of fluid that is used to disperse the particles will be lower, because it does not also have to be sufficient to fill an evacuated dispersion chamber. As a result, the particles can be dispersed to a sufficient extent to achieve a good spread of particles on a sample-collection surface but without dispersing a large proportion of the sample against the walls of the dispersion chamber. An added benefit is that the dispersion operation is easier to prepare and carry out if it is not necessary to evacuate the dispersion chamber. In effect, it need merely be closed off to prevent particles from escaping.

In an embodiment, the housing comprises a bell and the apparatus further includes a mechanism for positioning a sample collection surface in a position facing the base of the bell and a mechanism for causing relative movement between the sample collection surface and the bell so as to position the base against the sample collection surface.

An effect is that the collection means presenting the sample collection surface is easier to remove without disturbing the sample collected on it. This reduces the risk of contamination of the dispersion chamber or more generally the apparatus by the sample, as well as allowing the homogeneity of dispersion of the sample to be preserved more easily during subsequent transport of the collection means.

An embodiment of the apparatus includes an x-y stage, preferably an x-y-z stage, of an imaging system integrated with the apparatus.

An imaging system is a system for forming an image, i.e. an optical appearance or counterpart produced by exposing at least part of the collected dispersed sample to light or other radiation. An effect of this embodiment of the apparatus for dispersing the sample of particulate material is that an operator need not lift the collection means presenting the sample collection surface out of the apparatus for dispersing the sample. Controlled movement of the sample collection means out of the apparatus is allowed. The sample collection surface can remain generally horizontal. Where the x-y stage is the x-y stage or x-y-z stage of an imaging system, the means on which the dispersed sample has been collected need not be transported by hand over any distance to the imaging system for subsequent analysis. In particular where use is made of an x-y-z stage, the collected sample can subsequently be brought into focus more easily, and can also be moved further away from any part of the dispersion chamber. An added effect is the potential for automation of the process of sample dispersion and imaging of the dispersed sample. Typically, this may take up to twenty minutes, during which time the presence of an operator would not be required. The automation may involve the use of a standardised operating procedure, selectable by an operator in advance of the process of dispersion and imaging. The use of a single standardised operating procedure is advantageous, because the set-up of the assembly can be performed more efficiently. A further advantage is that the reproducibility is improved, since the dispersed sample will have a consistent orientation relative to the imaging system.

In an embodiment, a nozzle is provided at a position, in use, between the carrier and the inlet.

The nozzle allows to control the flow field of the volume of fluid passed past the carrier. By these means, the dispersion pattern of the particles can also be influenced.

In an embodiment, the nozzle is included in a replaceable module and the apparatus is arranged to allow mounting of the replaceable module.

An effect is that the flow field can be chosen to suit the type of particles being dispersed, through an appropriate choice of nozzle geometry.

In an embodiment, the nozzle is one of:
a convergent-divergent nozzle; and
a cylindrical nozzle.

An effect of using the convergent-divergent nozzle is that the kinetic energy of the fluid is increased to effect a relatively good separation of the particles. This can be useful where the particulate material is "sticky", but not very fragile. In other circumstances, the cylindrical nozzle is more effective at creating a dispersing shear flow field.

An embodiment, of the apparatus includes an upstream disc, configured to rupture at a certain pressure differential across the disc, wherein the apparatus is configured to allow placement of the disc in a position upstream of the carrier in a duct for supplying the volume of fluid.

An effect is that the carrier having the sample-bearing surface is subjected to a relatively sharp pressure pulse of well-defined amplitude.

In an embodiment, the upstream disc is configured to rupture at a higher pressure differential than the pressure differential sufficient to remove the sample-bearing surface from contact with the sample.

An effect is to ensure that the carrier is only subjected to a pressure pulse of high enough amplitude to effect a clean separation of the sample from the sample-bearing surface on which it has been placed. Thus, the dispersion process is controlled relatively effectively.

An embodiment of the apparatus for dispersing a sample of particulate material is configured to accommodate a replaceable sample carrier comprising the carrier having the sample-bearing surface and the upstream disc in the path of flow of fluid conducted, in use, by a duct in fluid connection with the inlet.

An effect is that complete off-line sample preparation is possible. It is relatively easy to avoid contamination of the sample. It is also relatively easy to avoid loss of sample. This can be of advantage where a controlled amount of the sample is to be dispersed, or where the sample comprises hazardous material.

According to another aspect of the invention, there is provided an assembly for particle analysis, including an apparatus for analysis of particles deposited on a sample collection surface and an apparatus for dispersing a sample of particulate material according to the invention.

The assembly for particle analysis includes at least one of an apparatus for measuring the size, an apparatus for measuring the shape and an apparatus for measuring the chemical composition of particles in a sample. The apparatus for dispersing a sample particulate material is suitable for providing a sample dispersed relatively homogeneously in a controlled manner, with a low likelihood of break-up of particles. Thus, the quality of the particle size analysis is improved, with the results providing a relatively reliable and accurate characterisation of the original sample of particulate material. This effect is achieved in particular where an apparatus for optical particle analysis is used, since a well-dispersed sample reduces the risk of taking a cluster of particles for a single particle.

In an embodiment, the apparatus for particle analysis includes a device for imaging a dispersed sample of particulate material on a sample collection surface of a collection means,
the housing of the apparatus for dispersing a sample of particulate material comprises a bell, and
the assembly further includes a mechanism for moving a collection means provided in the assembly between a position in which the sample collection surface faces the base of the bell and a position within a field of view of an imaging device.

An effect is that the collection means need not be moved by hand from the apparatus for particle analysis to the device for imaging the dispersed sample. The relatively homogeneous dispersion is therefore maintained, making for relatively accurate and repeatable measurements of the particle sizes or particle size distribution. A further effect is that any bias resulting in a pattern in the particle distribution is imaged consistently at the same location.

An embodiment includes a stage configured to support a collection means having a sample collection surface of sufficiently large dimensions as to cover the base of the bell to form the dispersion chamber.

An effect is that the quantity of dispersed particulate material can be determined relatively accurately, since it can be determined during preparation of the sample. Where a determination of the quantity of dispersed particulate material, e.g. by weighing, is dispensed with, one can rely on the quantity of dispersed sample corresponding relatively closely to the quantity determined during sample preparation. Also, the time between measurements is shorter, since less cleaning is required.

In an embodiment, the mechanism is further arranged to position the collection means in a direction substantially normal to its sample collection surface.

An effect is that the sample collection surface can be moved away from the bell mechanically, and can be brought into focus in the field of view of the imaging device.

According to another aspect, the method of dispersing a sample of particulate material according to the invention is characterised by passing a volume of fluid through the fluid duct by subjecting the carrier to a pulsed positive pressure differential relative to the dispersion chamber.

An embodiment includes controlling the volume of fluid through the fluid duct to influence characteristics of a dispersing shear flow established upon removal of the sample-bearing surface from contact with the sample.

An effect is to be able to establish a flow field appropriate to the characteristics of the sample to be dispersed.

In an embodiment, the dispersion chamber contains a fluid to at least an amount equivalent to the amount of air at ambient pressure at room temperature prior to the volume of fluid being passed through the fluid duct.

The absence of a (technical) vacuum in the dispersion chamber implies that the sample is dispersed into a dispersion chamber filled with a non-negligible amount of fluid. In practice, this will be gas or a gas mixture, such as air. The absence of a (technical) vacuum means that the dispersed particles are decelerated. This reduces the force on impact with the surface on which the dispersed sample is collected. The dispersion operation is relatively easy to carry out, and the volume of fluid used to disperse the sample of particles is relatively low.

An embodiment of the method includes tailoring at least part of a pressure pulse to which the carrier is subjected to conform to at least one of a pre-determined profile or peak value.

The pre-determined profile or peak value can be selected to achieve a particular aim, e.g. primarily to avoid shattering of particle on surfaces in the dispersion chamber, or to achieve a higher degree of dispersion. Tailoring at least part of a pressure pulse to conform to at least one of a pre-determined profile or peak value makes each dispersion operation more accurately repeatable. In a particular embodiment, the carrier comprises a membrane and the pressure pulse is tailored to have a profile with a gradient sufficiently low for the membrane to rupture at a certain rupture pressure. Each such membrane will rupture at substantially the same static pressure difference across the membrane only if mounted in consistently the same, time-invariant, way. Where this cannot be guaranteed, the pressure profile with the low gradient allows for the use of a relatively slow feedback loop to detect the rupture and close off the fluid supply. This increases the repeatability of the dispersion operation, using a minimum of fluid for the dispersion.

In an embodiment, the method includes the use of an apparatus according to the invention and/or an assembly according to the invention.

According to another aspect of the invention, there is provided a membrane for use in an apparatus according to the invention, wherein the carrier includes a membrane, arranged to rupture upon application of a sufficient pressure differential across the membrane. The membrane is electrically conducting.

An effect is to facilitate earthing of a sample of particulate material placed on the sample-bearing surface of the carrier, in use. Thus, the electric charge on the particles is greatly reduced before they are dispersed.

According to another aspect of the invention, there is provided a set of membranes for use in an apparatus according to the invention, wherein the carrier includes a membrane, arranged to rupture upon application of a sufficient pressure differential across the membrane. At least some of the membranes are arranged to rupture at different respective values of the pressure differential.

An effect is to allow adaptation of the dispersion process to the type of particulate material being dispersed by appropriate choice of one of the set of membranes. A pulsed pressure differential of appropriate amplitude is used in conjunction with the chosen membrane.

According to another aspect of the invention, there is provided a sample carrier for use in an apparatus according to the invention, wherein the carrier includes a membrane, arranged to rupture upon application of a sufficient pressure differential across the membrane, and the apparatus includes the apparatus including a fitting for receiving a module supporting the membrane in the path of flow of fluid conducted, in use, by a duct in fluid connection with the inlet, the fitting including a mechanism for engaging the module such as to hold the module in a pre-determined orientation, wherein the sample carrier is configured to function as the module supporting the membrane.

An effect is that the sample carrier is suitable for preparing a sample for dispersion away from the apparatus.

An embodiment of the sample carrier further includes an upstream disc, configured to rupture at a certain pressure differential across the disc, the sample carrier being suitable for placement in the path of flow in such an orientation that the disc is positioned upstream of the membrane.

An effect is that the membrane is subjected to a pressure pulse of relatively precisely controlled amplitude, and having a profile exhibiting a relatively sharp leading edge. These effects contribute to controlled, repeatable dispersion of the sample. A further consideration is that the need for a pump or valve with consistent and sufficiently fast response times is obviated. A further effect is that the disc and membrane, together with the module supporting them, are easily configured to enclose the sample, preventing loss or contamination of the sample, or indeed contamination of the environment by the sample.

In an embodiment, the disc is configured to rupture at a higher pressure differential across the disc than that across the membrane at which the membrane is arranged to rupture.

An effect is to ensure with a relatively high degree of certainty that the membrane will rupture, and in the intended manner. The disc assures that a pressure pulse with a desired profile is provided.

According to another aspect of the invention, there is provided a kit of parts for use in an apparatus according to the invention wherein the carrier includes a membrane, arranged to rupture upon application of a sufficient pressure differential across the membrane, which kit includes at least one membrane and a set of rigid supports for the membrane each support including a central aperture of a different respective size. An effect of the supports is to regulate the pressure differential at which the membrane, when supported by one of the rigid supports, bursts. Thus, only one or a limited range of membranes need be provided to provide a choice of pressure differentials at which the sample-bearing surface of the carrier is removed from contact with the sample.

According to another aspect of the invention, there is provided a set of replaceable modules for use in an apparatus according to the invention, wherein a nozzle is provided at a position, in use, between the carrier and the inlet and wherein the nozzle is included in a replaceable module and the apparatus is arranged to allow mounting of the replaceable module. Each of the set of replaceable modules includes a nozzle of different dimensions and/or geometry.

An effect is to place the sample in a flow field depending on the choice of module, that is to say nozzle dimensions and/or geometry. Thus, the flow field can be adapted to the type of sample to be dispersed.

The invention will now be explained in further detail with reference to the accompanying drawings, in which.

Figure 1:
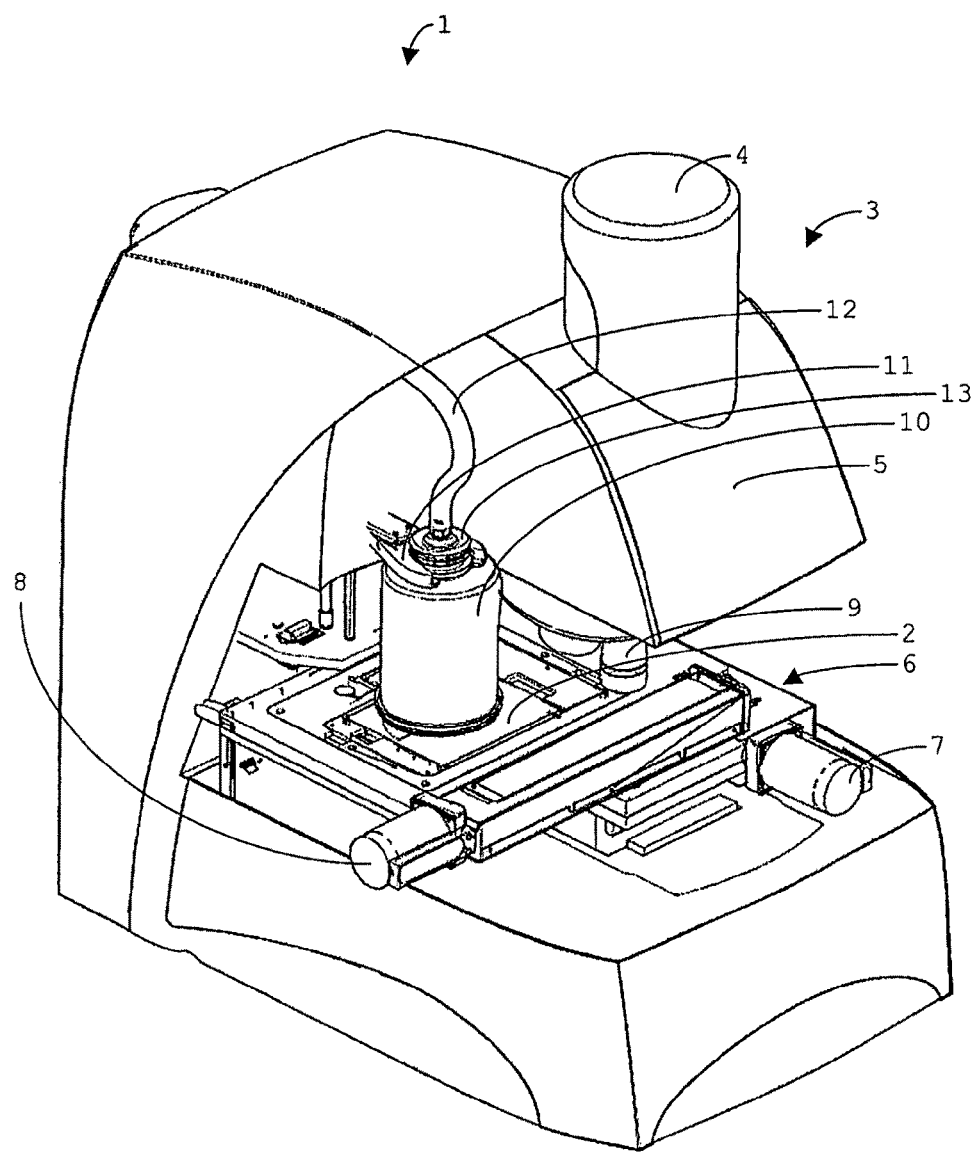
FIG. 1 is a schematic perspective view of an assembly for particle size analysis.

An assembly 1 for particle size analysis includes an apparatus for optical particle size analysis of particles deposited on a specimen plate 2 and an apparatus for dispersing a sample of particulate material onto the specimen plate 2. The specimen plate 2 is of a generally rectangular shape, of sufficiently large dimensions that a circle with a diameter of approximately 80 mm could be inscribed within its edges. Other values and/or geometries are possible. In this example, the apparatus for optical particle size analysis includes a device 3 for imaging a sample of particulate material on a sample collection surface of a collection means, including a digital camera 4 and microscope 5. To determine the sizes of particles on the specimen plate 2, an X-Y-Z stage 6 is provided. First and second motors 7,8 are provided to position stage on which a specimen plate 2 has been placed in the X and Y directions in a plane generally perpendicular to the optical axis of a microscope objective 9 being used. In this embodiment, positioning of the stage in the Z-direction, parallel to the optical axis of the microscope objective 9 is also possible. In other embodiments, this can be dispensed with, with only the microscope objective 9 being movable in the Z-direction.

Particle sizes are determined by imaging the particles on the specimen plate 2 carried by the X-Y-Z stage 6, and analysing the images to distinguish between individual particles. The sizes of these individual particles are calculated by determining the number of pixels occupied by the particle images and translating this to a physical size using the known magnification of the microscope 5. The area to scan is selected on the basis of the number of particles required to give a statistically significant result. A sub-area of the sample collection surface of the specimen plate 2 can be chosen substantially at random, since the apparatus for dispersing the particulate material is tailored to avoid spatial bias.

Although optical particle size and morphological analysis is used herein as an example, the techniques outlined herein are equally applicable to assemblies for optical analysis of the particle composition, for example. Such assemblies include an apparatus similar to the device 3, but provided in conjunction with a broadband illumination source and tuneable filters so that the image contrast can be manipulated by selection of wavelengths in which specific species of the particles have absorption bands. This allows the contrast to be enhanced for that species, which allows composition identification.

Examples of an apparatus for optical particle size and morphology analysis as discussed briefly above are known as an independent device. Other types of apparatus can be used instead, such as those measuring the diffraction of light or non-visible electromagnetic radiation by the particles. Such types of apparatus are also known per se. In conventional apparatus, the collection means with the sample collection surface carrying the dispersed sample is placed on the X-Y-Z stage. The sample is dispersed onto the sample collection surface in a separate device.

The assembly 1 for particle size analysis represents an alternative in which the apparatus for optical particle size analysis and the apparatus for dispersing a sample of particulate material are integrated, sharing components and operating under a single control system. The control system is implemented in the form of a computer (not shown). Using the control system, the operations of preparing a dispersed sample and measuring the particle sizes are combined, in the sense that the operator need not set them up separately. Instead, a single sample can be placed in the assembly, dispersed and then measured. Standard operating procedures (SOPs) can be defined to unify selection of parameters governing both processes.

The X-Y-Z stage 6 is operative to move the specimen plate 2 with the dispersed sample from the apparatus for dispersing a sample of particulate material to a position in the field of view of the device 3 for imaging a sample of particulate material. Because the mechanism for moving the X-Y-Z stage 6 is further arranged to position the stage carrying the specimen plate 2 in a direction substantially normal to the sample collection surface of the specimen plate 2 carrying the dispersed sample, it can be brought into focus, as well as being brought out of reach of components of the apparatus for dispersing the sample.

In the illustrated embodiment, movement of the specimen plate 2 is further facilitated in that a dispersion chamber of the apparatus for dispersing the sample of particulate material if formed by a housing comprising a bell 10. That is to say that the housing has the shape of a deep inverted cup, open to one side. The specimen plate 2 is of sufficiently large dimensions as to close off the bell 10 when the latter is brought down with a seal (not shown) at the edges of its base in contact with the surface of the specimen plate 2. Thus, a dispersion chamber is formed of which, on the inside, the base is provided only by the specimen plate 2. The entire dispersed sample is therefore collected on the sample collection surface of the specimen plate 2. When the sample has been dispersed onto the specimen plate 2, the bell 10 and specimen plate 2 are separated, and the X-Y-Z stage 6 is moved from a position in which the specimen plate 2 faces the base of the bell 10 to a position within the field of view of the device 3 for imaging the dispersed particles.

Figure 7:
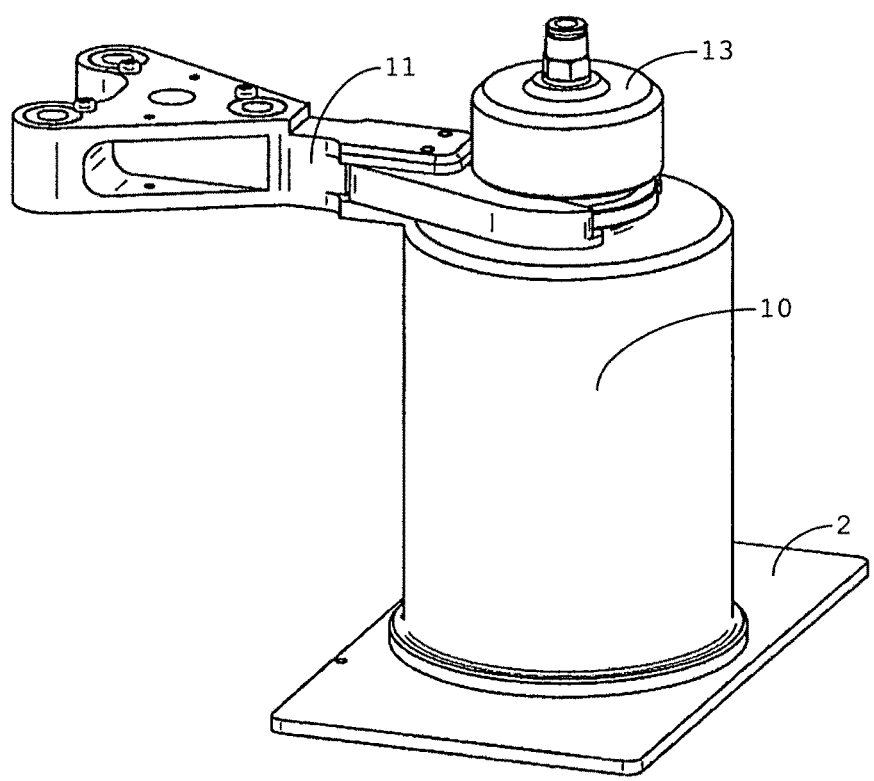
FIG. 7 is a schematic perspective view of a housing for forming a dispersion chamber, wherein the housing comprises a bell.
Figure 8:
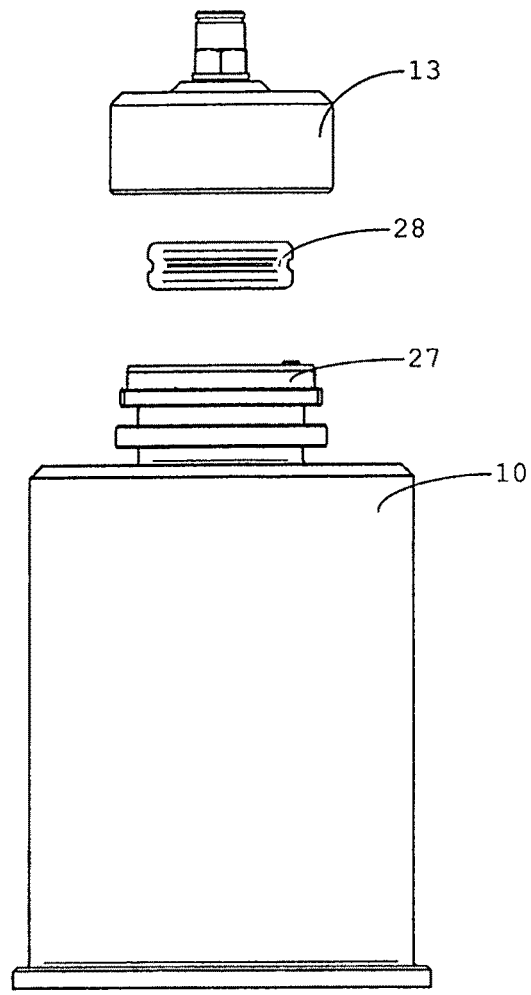
FIG. 8 is a schematic exploded plan view of the bell, a sample carrier for use in the dispersion apparatus, and a fitting for connecting a source of compressed gas.
Figure 9:
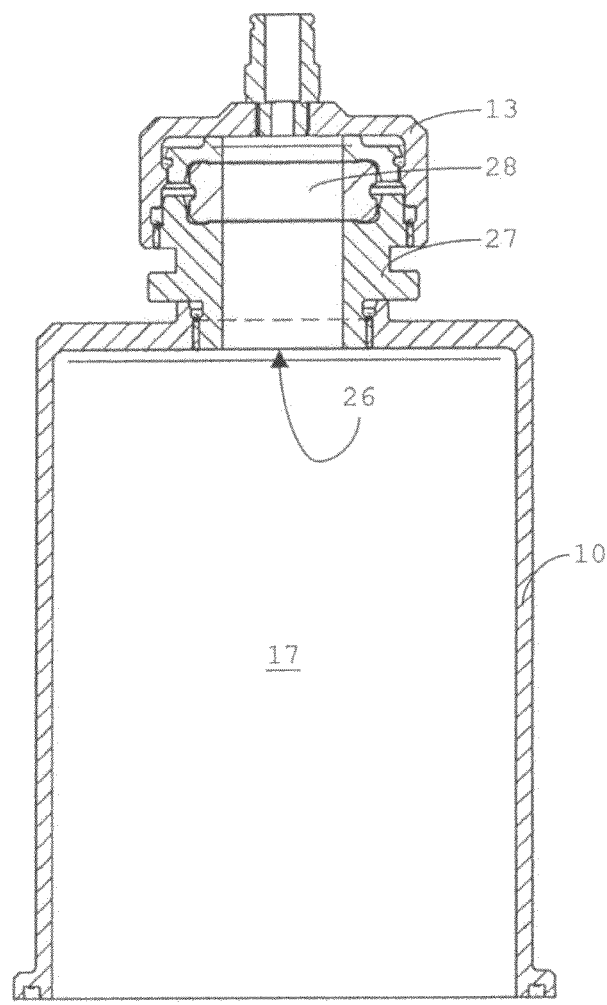
FIG. 9 is a schematic cross-sectional view of the components illustrated in FIG. 8.
Figure 10:
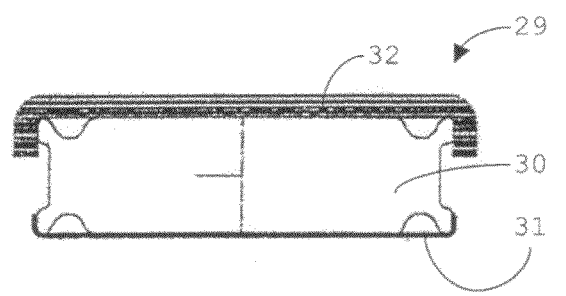
FIG. 10 is a schematic plan view of a first embodiment of a sample carrier.
Figure 11:
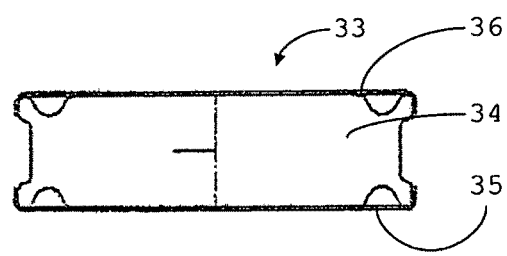
FIG. 11 is a schematic plan view of a second embodiment of a sample carrier.
Figure 12:
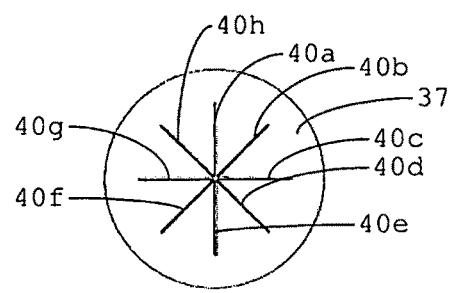
FIG. 12 is a schematic view of a first embodiment of a membrane for use in a sample carrier according to FIG. 10 or FIG. 11.
Figure 13:
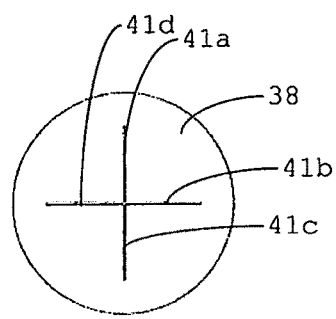
FIG. 13 is a schematic view of a second embodiment of a membrane for use in a sample carrier according to FIG. 10 or FIG. 11.

The bell 10 is suspended by a support clamp 11 (see also FIG. 7). An actuator system is provided for moving the support clamp 11 in a direction generally normal to the base of the bell 10. Thus, the bell 10 and the specimen plate 2 can be separated by moving the support clamp 11 and/or the stage 6 in the Z-direction, generally normal to the sample-bearing surface of the specimen plate 2.

Turning to the apparatus and method for dispersing a sample of particulate material, they fall within the category of dry dispersion mechanisms. Such a mechanism avoids problems associated with wet dispersion mechanisms, such as the risk that the dispersant affects the particle properties. Dry dispersion mechanisms require controllable application of dispersive energy to separate bulk powder or droplets into individual particles for measurement.

As outlined herein, dispersive energy is provided by subjecting a carrier having a sample-bearing surface on which the sample to be dispersed has been placed to a pulsed positive pressure differential relative to the dispersion chamber. To this end, a volume of fluid is passed through a fluid supply line 12 connected to an inlet at the top of the bell 10 by means of a fitting 13.

Figure 2:
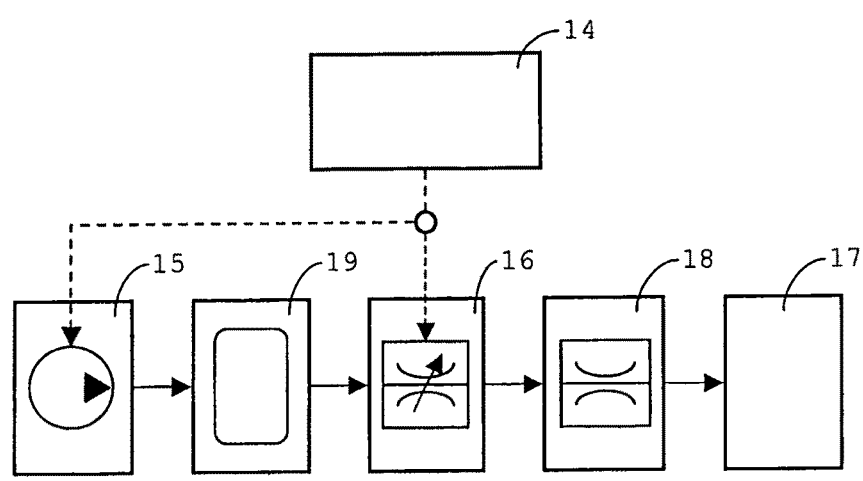
FIG. 2 is a block diagram illustrating components of an apparatus for dispersing a sample of particulate material, comprised in the assembly of FIG. 1.

FIG. 2 shows, in the form of a block diagram, some components of the apparatus for dispersing a sample of particulate material, suitable for dispersing samples with particle sizes at a value or in a range of values in the range of approximately 0.5 μm to 300 μm. A controller 14, comprised in or connected to the control system for the entire assembly 1, controls the operation of a pump 15 and a valve 16. The pump 15 and valve 16 are operable to subject a carrier (not shown in FIG. 2) having a sample-bearing surface on which a sample of particulate material has been placed, to a pulsed positive pressure differential relative to the dispersion chamber 17. In the illustrated embodiment, the carrier is removably arranged at a position between the valve 16 and a nozzle 18. A plenum 19 is provided between the pump 15 and the valve 16, in some embodiments simply in the shape of a conduit.

The pump 15 is used to pressurise the fluid used as a dispersant, suitably a gas or a gas mixture. In one embodiment, the gas is conditioned, for example dehumidified. Suitable gases or mixtures include air and nitrogen. The choice will depend at least partly on the type of particulate material to be dispersed. It is observed that alternative embodiments of the apparatus comprise a reservoir of pre-compressed fluid in the place of the pump 15 and the plenum 19.

The valve 16 is used to provide the pulse, that is, to regulate the passage of fluid such that a certain volume, metered by the valve 16, is passed. The pressure profile is pulsed in the sense that it rises and falls again. In the embodiment to be described, the pulse, by which is meant the time-varying pressure profile, is further shaped by components of the sample carrier. As a result, the response times of the valve 16, and to a lesser extent those of the controller 14, are less critical than would otherwise be the case. The valve 16 and controller 14 are used to control the volume of fluid that is passed past the carrier. The target volume is adjusted to influence the shear flow characteristics that determine how the sample is dispersed. In an embodiment, the target volume is selected in dependence on the type of sample to be dispersed.

It is observed that a vacuum pump is absent from the diagram of FIG. 2. In the illustrated embodiment, the dispersion chamber 17 is formed by bringing the bell 10 into contact with the specimen plate 2, so that the dispersion chamber 17 is at ambient pressure. The pulsed positive pressure differential is also positive with respect to ambient pressure. In other embodiments, a partial vacuum may be established in the dispersion chamber 17.

FIGS. 3-6 show the results of simulations carried out using a computational fluid dynamics package. The drawings show the effects of the use of a dispersion chamber 17 containing an amount of air sufficient to establish a pressure level substantially superior to a technical vacuum compared to the pressure levels used in a known device for dispersing a sample of particulate material. In the known device, the sample is placed on a membrane, and the dispersion chamber is evacuated until the pressure is low enough for the membrane to rupture. At this point, air rushes in with the sample, which is dispersed.

Figure 3:
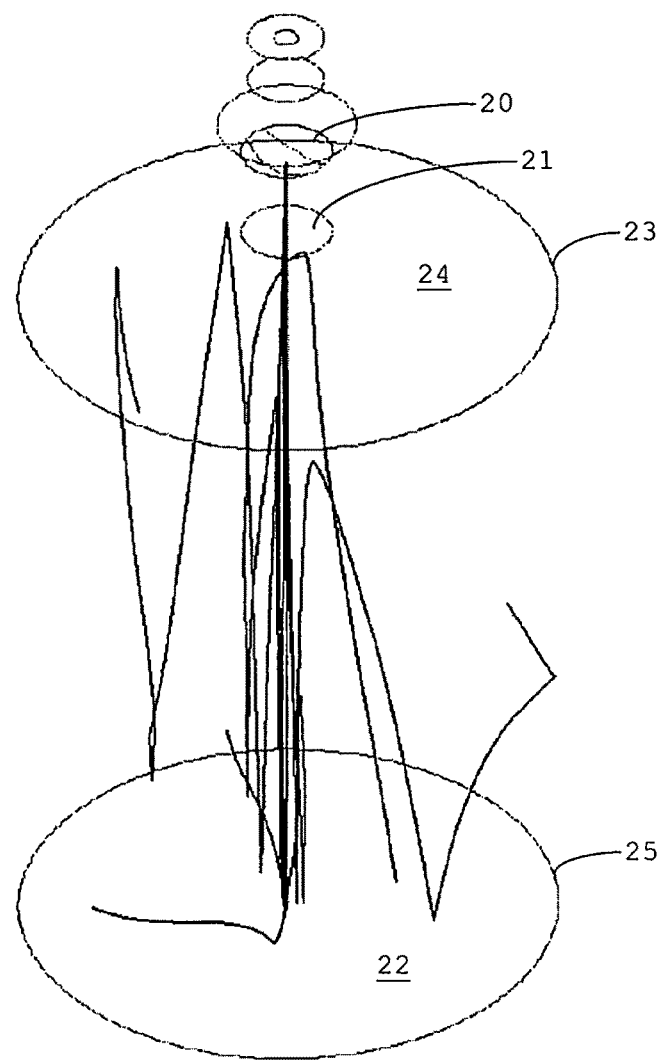
FIG. 3 is a schematic illustration of the results of a two-phase flow simulation of the effects of dispersing a sample into an evacuated dispersion chamber.
Figure 4:
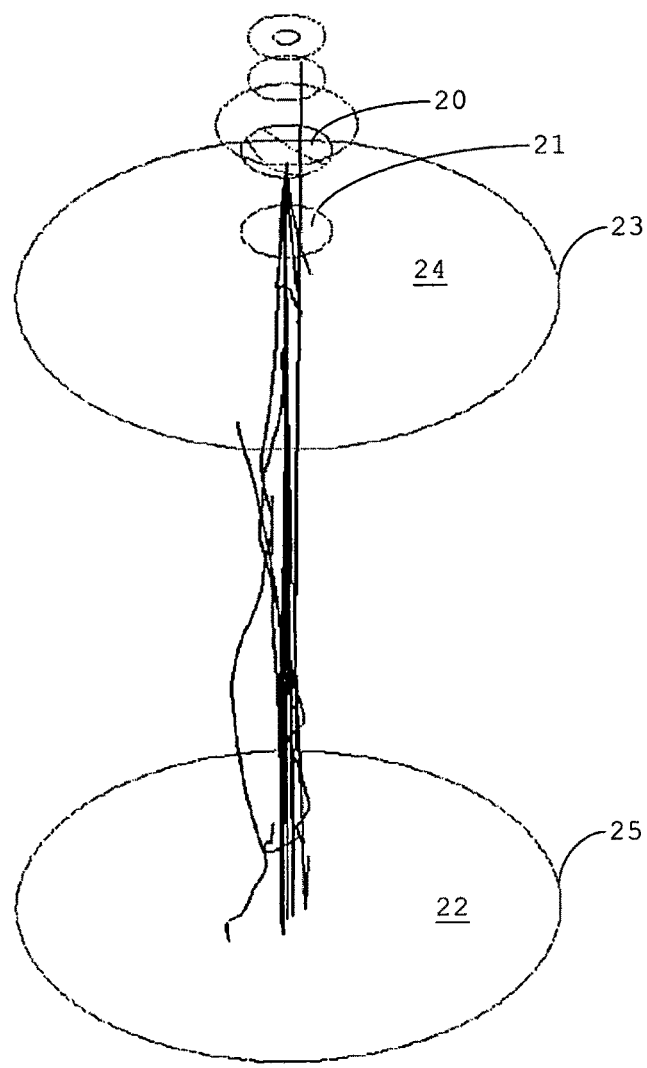
FIG. 4 is a schematic illustration of the results of a two-phase flow simulation of the effects of dispersing a sample into a dispersion chamber filled with air at ambient pressure.

The simulations modelled the flow of fluid and particles as a two-phase flow. FIGS. 3-6 show only details of the flow of the particle phase, not also the fluid flow. Only the trajectories of selected particles are illustrated in FIGS. 3 and 4. The sample is placed on a sample-bearing surface of a carrier 20. The carrier 20 is arranged such that the sample-bearing surface is removed from contact with the sample upon application of a sufficient pressure differential across the carrier 20 between the sample-bearing surface and an opposite side of the carrier 20. Of the dispersion chamber 17, only an inlet 21 and a sample-collection surface 22 are shown. Sidewalls extend between an edge 23 of a ceiling 24 of the dispersion chamber 17 and an edge 25 of the sample-collection surface 22. FIG. 3 illustrates the results of a simulation in which the dispersion chamber 17 is evacuated to establish a partial vacuum sufficient to rupture a membrane forming the carrier 20, thus removing the sample-bearing surface of the carrier 20 from contact with the sample. FIG. 4 illustrates the results of a simulation in which the dispersion chamber 17 is maintained at ambient pressure. Both FIG. 3 and FIG. 4 depict the situation at 50 ms from removal of the sample-bearing surface of the carrier 20 from contact with the sample. The particle trajectories in FIG. 3 indicate that particles traverse the dispersion chamber 17 several times as they bounce off the sidewalls and sample collection surface 22. By contrast, the particles are much more likely to follow a straight path through the inlet 21 to the sample-collection surface 22 if there is no vacuum in the dispersion chamber 17.

Figure 5:
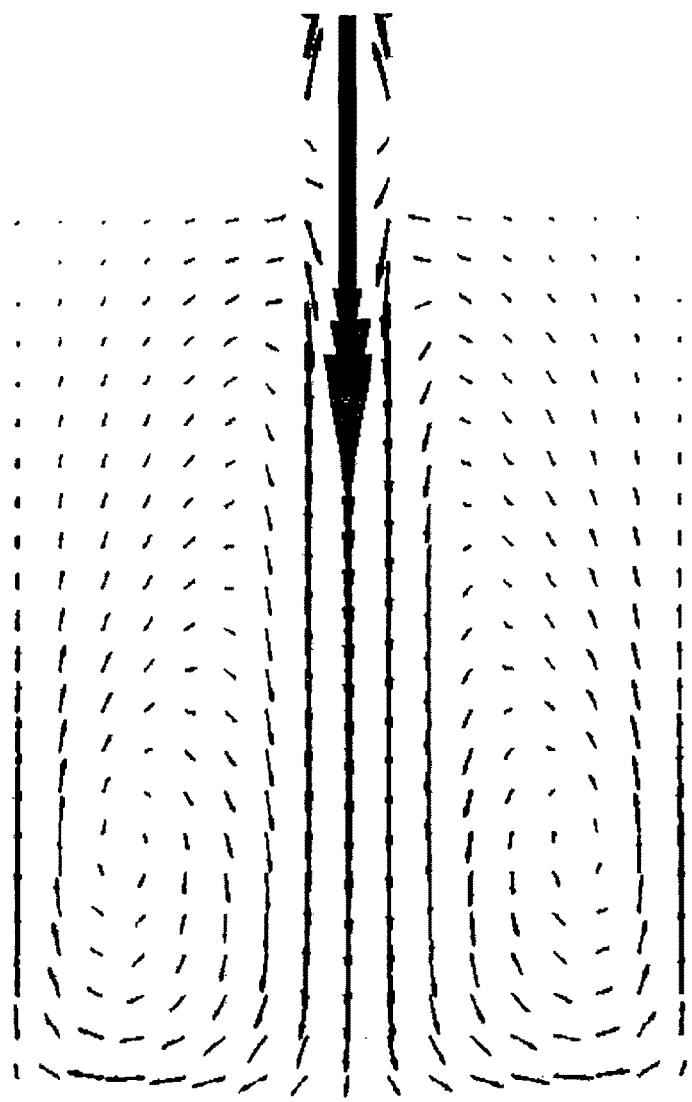
FIG. 5 is a vector diagram affording a cross-sectional view of the mean particle flow field 5 ms into the simulation also illustrated in FIG. 3.
Figure 6:
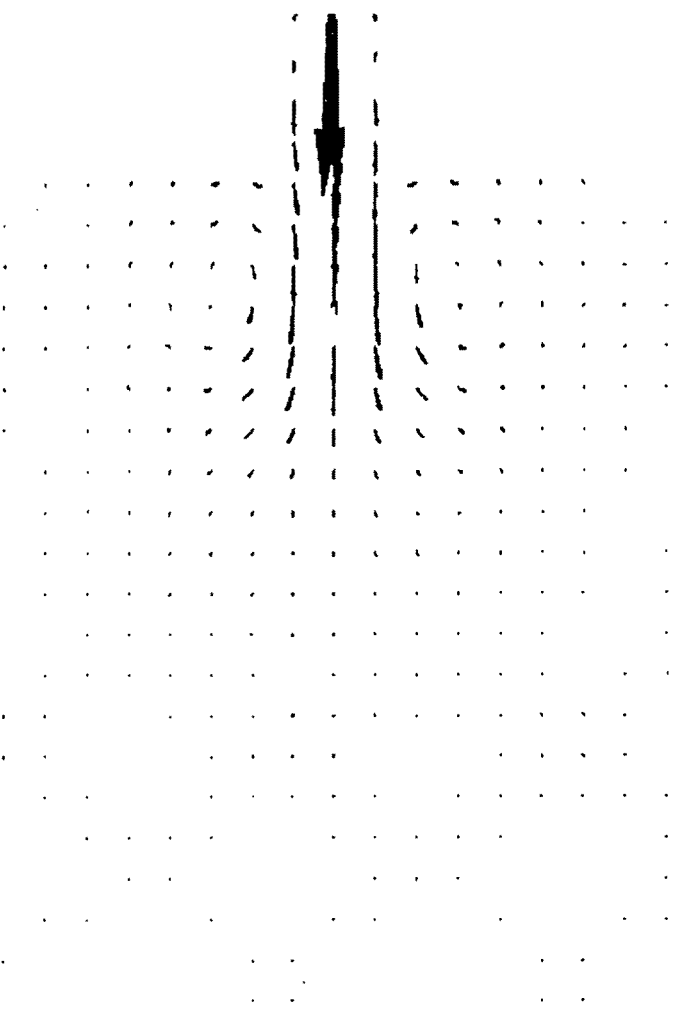
FIG. 6 is a vector diagram affording a cross-sectional view of the mean particle flow field 5 ms into the simulation also illustrated in FIG. 4.

Vector diagrams in FIGS. 5 and 6 afford a cross-sectional view of the mean particle velocity distribution 5 ms after removal of the sample-bearing surface of the carrier 20 from contact with the sample. The drawings illustrate the velocity that a particle would have if it were to be present at one of the grid positions for which the velocity is indicated. FIG. 5 depicts the situation where the sample is dispersed against vacuum, whereas FIG. 6 illustrates the velocity field upon dispersion against ambient pressure. It is clear that the velocity field in FIG. 5 is likely to result in more particles breaking up before reaching the sample-collection surface 22.

Returning to the constructional details of the embodiment introduced in FIG. 1, FIGS. 7-9 illustrate the formation of the dispersion chamber 17 by means of the bell 10 and the specimen plate 2 (not visible) on the X-Y-Z stage 6. The dispersion chamber 17 has an inlet 26 facing the sample collection surface of the specimen plate 2, in use. In the illustrated embodiment, a central axis of the inlet 26 is generally aligned with a normal of the sample collection surface of the on the base of the bell 10, in use.

The fluid supply from the valve 16 is provided by means of the fluid supply line 12 attached to the fitting 13. The fitting 13 can be releasably secured to the bell 10, or to a module comprising a nozzle, as will be shown. A fitting 27 provided at the inlet 26 of the dispersion chamber 17 and integral with the bell 10 co-operates with the fitting 13 to receive a module 28 supporting a membrane (not shown). The membrane has a sample-bearing surface on which the sample to be dispersed has been placed. Thus, the module 28 is received in the path of flow of fluid conducted, in use, by a duct in fluid connection with the inlet 26. The membrane is arranged to rupture upon application of a sufficient pressure differential across it, so that it is removed from contact with the sample. The sample is entrained and/or propelled into the dispersion chamber 17 by the volume of fluid passed through the membrane.

In an embodiment, one or both of the fittings 13,27 are provided with a mechanism engaging with the module 28 in such a manner that the module is held in a pre-determined orientation about a central axis. Thus, where two samples are dispersed using membranes of the same type, the pattern of rupture of the membrane will be the same relative to a co-ordinate system attached to the sample collection surface. This helps to ensure repeatability of measurements made on the dispersed sample collected on the sample collection surface of the specimen plate 2. It will be recalled that the specimen plate 2 remains on the X-Y-Z stage 6 as it is moved into the field of view of the device 2 for imaging the sample, so that repeatability is indeed assured.

In the illustrated embodiment, at least one of the fittings 13,27 for receiving the module 28 supporting the membrane is such as to be in electrically conducting contact with at least the membrane. A further electrical connection can be provided via the support clamp 11 to earth.

FIG. 10 shows a single-disc sample carrier 29, including a module 30 for supporting a membrane 31. The membrane 31 fulfils the role of a carrier having a sample-bearing surface on which to place the sample of particulate material to be dispersed. The membrane 31 allows the sample to be placed centrally in the flow of fluid that disperses the sample. A cap 32 closes off the single-disc sample carrier 29 after the sample has been placed on the membrane 31. The cap 32 is removed upon placement of the single-disc sample carrier 29 in the fitting 27 of the bell 10. Thus, the sample is not lost, and cannot contaminate the environment of the apparatus for dispersing it. Nevertheless, the single-disc sample carrier 29 is intended primarily for use with non-hazardous samples. Since the speed at which the membrane 31 ruptures is determined by the response time of the valve 16 the single-disc sample carrier 29 is primarily suitable for dispersing samples requiring a low intensity of dispersion energy.

FIG. 11 shows a dual-disc sample carrier 33 comprising a module 34, a membrane 35 and an upstream disc 36. The upstream disc 36 is configured to rupture at a certain pressure differential across the upstream disc 36. In use, the dual-disc sample carrier 33 is assembled with the assembly 1, such that the upstream disc 36 is in a position upstream of the membrane 35, i.e. the carrier with the sample-bearing surface. The upstream disc 36 is configured to rupture at a higher pressure differential than the pressure differential at which the membrane 35 is configured to rupture. In one embodiment, the module 34 is dimensioned such that the membrane 35 and upstream disc 36 are spaced apart at a distance sufficient to avoid contact of parts of the ruptured upstream disc 36 with any sample placed on the membrane 35. In an example, the upstream disc 36 is placed at least twice the distance sufficient to avoid any contact between the upstream disc 36, when ruptured, with the membrane 35 itself. In an alternative embodiment, the module 34 is dimensioned such that the membrane 35 and upstream disc 36 are spaced apart at such a distance that at least central parts of the ruptured upstream disc 36 move towards and past the position of the membrane 35 upon rupture. The upstream disc 36 thus deforms through the membrane 35.

The upstream disc 36 is operable to provide the pressure pulse with a steeper rising flank, and to define the amplitude more accurately. This helps to make the dispersion operation and subsequent particle analysis repeatable with relatively good consistency of results. Performance is independent of the performance of the valve 16.

The properties of the modules 30 and 34 of the single-disc and dual-disc sample carriers 29,33 are generally as described for the module 28 shown in FIGS. 8 and 9. The properties of the module 34 are such as to allow the upstream disc 36 to be attached to it, e.g. mechanically or by gluing, upon placement of the sample to be dispersed on the sample-bearing surface of the membrane 35.

Regardless of whether the single-disc or dual-disc sample carrier 29,33 is used, due to the fact that they are removable from the sample dispersion apparatus, the sample can be measured and placed in the sample carrier 29,33 off-line, for example in a fume cupboard. It has been found that measuring spoons are usefully employed for preparing a sample with good repeatability. In an embodiment, a series of measurement spoons are provided, each of a certain volume, with guidance enabling a user to identify the correct amount of sample which will provide the optimum (lean) dispersion. In embodiments, the membranes 31,35 are provided with central dimples (not shown), in order to centre the sample with respect to the flow of fluid used to rupture the membranes 31,35.

In one, cost-effective embodiment, the membranes 31,35 are comprised of a simple unaltered piece of metal foil having a thickness of at least five micrometers. Such foil is generally available for use in manufacturing electronic components such as capacitors. In particular where the membranes 31,35 are subjected to a pressure pulse with at least one of a pre-determined pressure profile and a pre-determined peak value, reliable rupture at a pre-determined pressure differential and according to a reproducible pattern is achieved.

FIGS. 12-15 illustrate three further exemplary types of membranes 37,38,39 for use as the membrane 31,35 in the single-disc or dual disc sample-carriers 29,33. The same types of profiles can be used for the upstream disc 36. The membranes 37,38,39 are weakened mechanically to produce a pre-determined failure geometry and to rupture at a consistent pre-determined pressure differential. The membranes 37,38,39 are formed of a sheet of generally uniform thickness, weakened according to a pattern that is symmetric with respect to a normal to the sample-bearing surface. In this embodiment, they are circle-symmetric with respect to a normal centred on the sample-bearing surface, by being weakened along a plurality of line segments 40,41,42 extending in respective generally radial directions from the normal centred on the sample-bearing surface.

Embodiments with any number of radially extending line segments 40,41,42 are possible. A first membrane 37 has a larger number of line segments 40 than a second membrane 38. This configuration is suitable where the first membrane 37 is made of metal or a metal alloy, e.g. where it is made of Aluminium. The metal has a grain structure that means that it tends to give in a preferred direction. Having a larger number of radially extending line segments 40 ensures that at least one will lie close to the preferred direction, providing a more uniform burst pressure.

Due to the characteristic of metallic membranes, the membranes 37,38,39 will generally be made of a non-metallic material, if necessary laminated or coated with a thin metallic or otherwise electrically conducting layer. For membranes where the main material is non-metallic, the likelihood of the membrane being ruptured along all radially extending line segments 40,41,42 diminishes with an increasing number of such radially extending line segments. As soon as the membrane ruptures along one line segment, the pressure on the other line segments 40,41,42 is reduced. Since a failure along one of the radially extending line segments would reduce the symmetrical pattern of the dispersing shear flow, the number of radially extending line segments 40,41,42 will generally be lower than six, for example four or even the minimum: three.

Figure 14:
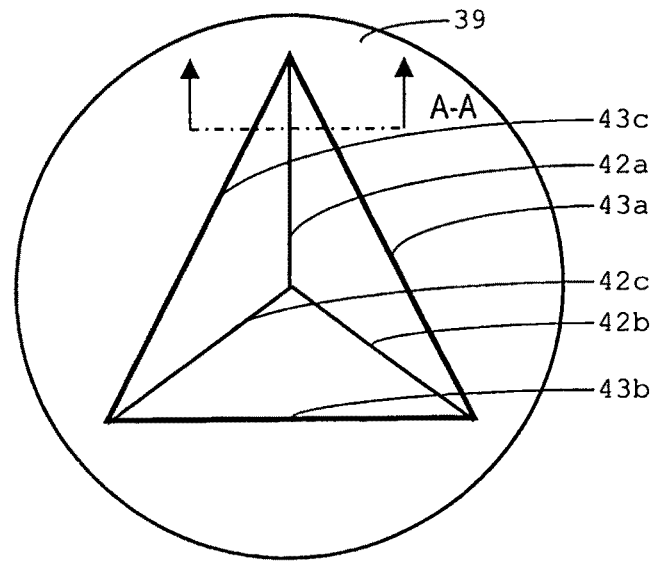
FIG. 14 is a schematic view of a third embodiment of a membrane for use in a sample carrier according to FIG. 10 or FIG. 11.
Figure 15:
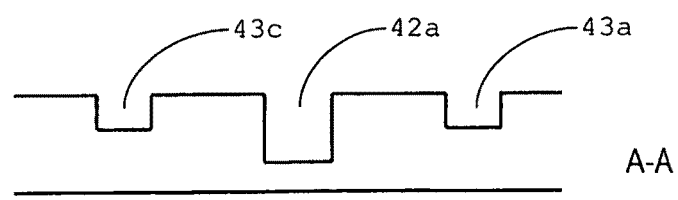
FIG. 15 is a partial cross-sectional view of the membrane according to FIG. 14.
Figure 16:
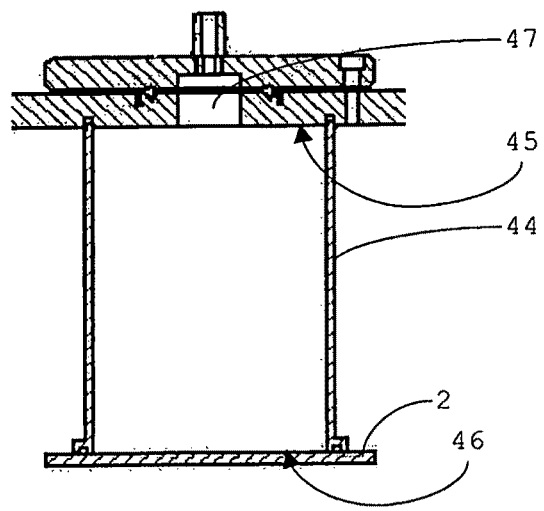
FIG. 16 is a schematic view of a first embodiment of a dispersion chamber.

A third membrane 39 (FIGS. 14 and 15) is weakened along at least three radially extending line segments 42. It is also weakened along line segments 43 connecting points removed from radially innermost end points on angularly neighbouring ones of the radially extending line segments 42. In the illustrated embodiment, the line segments 43 connect the outermost end points in radial direction of the radially extending line segments 42. As is illustrated in FIG. 15, the third membrane 39 is weakened to a lesser extent along the connecting line segments 43 than along the radially extending line segments 42. As a result, the third membrane 39 is configured to rupture along the radially extending line segments 42, whereas sections of the membrane between the radially extending line segments 42 remain attached at the connecting line segments 43. The latter function as hinges, ensuring consistent rupture patterns across a batch of the third membranes 39.

One way of weakening the membranes 37,38,39 is by scoring the sheet of generally uniform thickness along the line segments 40-43, respectively. Other methods include moulding, laser patterning, electroforming, photo-etching, etc.

It is contemplated that the membranes 37,38,39 be made electrically conductive, either intrinsically or by coating at least the sample-bearing surfaces thereof. As mentioned, the fittings 13,27 and support clamp 11 can provide an electrical connection to earth, so that the membranes 37,38,39 are earthed when placed in the sample dispersion apparatus. The effect is to reduce the tendency of the particles to move towards the walls of the dispersion chamber 17, as well as to help avoid the presence of electrostatically charged particles on the sample collection surface of the specimen plate 2 upon dispersion. Elongated charged particles have a tendency to "stand on end" on the sample collection surface of the specimen plate 2. Charged particles generally have a tendency to form chains. Both tendencies are combatted, making subsequent particle size analysis more accurate.

Powders can vary enormously in respect of their dispersability. Some are sticky and/or contain agglomerates and require significant dispersive energy to separate the particles. Other samples may be of a fragile crystalline type, with the particles fracturing easily if the dispersive energy is too excessive. Some powders are susceptible to acquiring static charge. It can therefore be desirable to adapt the size and/or shape of the pressure pulse to which the sample is subjected to the type of sample to be dispersed. To this end, a set of membranes 31,35,37,38,39 may be provided, at least some of which are arranged to rupture at different respective values of the pressure differential across them. Alternatively or additionally, at least some of them are arranged to rupture according to different respective patterns. Of course, the set can be provided in the form of a set of single-disc or dual-disc sample carriers 29,33 provided with different membranes 31,35. Moreover, there may be provided a set of dual-disc sample carriers 29,33 provided with upstream discs 36 arranged to rupture at different respective pressure differentials and/or according to different respective patterns.

In an alternative embodiment, a set of single-disc or dual-disc sample carriers 29,33 is provided with generally similar membranes 31,35. Rigid supports are provided for partially supporting a surface of the membranes 31,35 opposite the sample-bearing surface. The rigid supports each include a central aperture of a different respective size. The effect is substantially similar to the effect achieved by providing a set of differently configured membranes 31,35, in that the membranes 31,35 will rupture at different respective pressure differentials, depending on the size of the central aperture of the rigid support supporting them at their edges.

FIGS. 16-20 illustrate prototype configurations of dispersion chambers.

A first bell 44 has a generally circle-cylindrical shape, forming a dispersion chamber terminating in a generally plane ceiling 45 opposite a base 46. Likewise, an inlet duct 47 has a generally circle-cylindrically shaped configuration, forming a duct for receiving one of the sample carriers 29,33.

A second bell 48 is suitable for forming a dispersion chamber having a ceiling 49 tapering towards an inlet duct 50 which is divergent with respect to the direction of fluid flow. An effect is that fluid will pass the position of the sample-carrier at higher speed. The inlet duct 50 is positioned opposite a base 51, generally centred on a central normal of the base 51.

Figure 17:
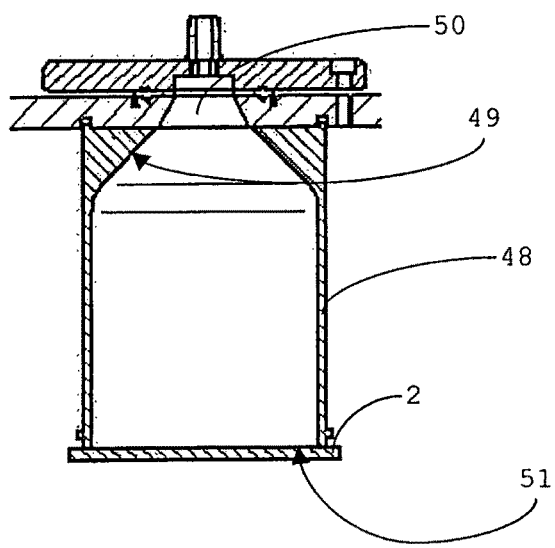
FIG. 17 is a schematic view of a second embodiment of a dispersion chamber.
Figure 18:
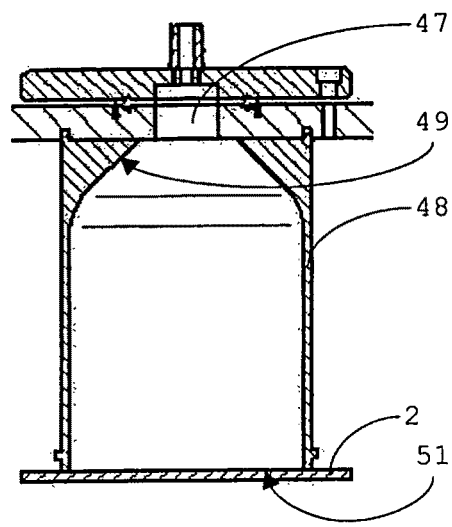
FIG. 18 is a schematic view of a third embodiment of a dispersion chamber.

FIG. 18 shows the second bell 48 in combination with the inlet duct 47 illustrated in FIG. 17. The fluid will enter the dispersion chamber at about the same speed as in the configuration of FIG. 16, but the flow pattern inside the dispersion chamber will be different, in particular less turbulent in the vicinity of the inlet duct 47. This can be desirable for lighter particles or particles with little tendency to adhere to one another.

Figure 19:
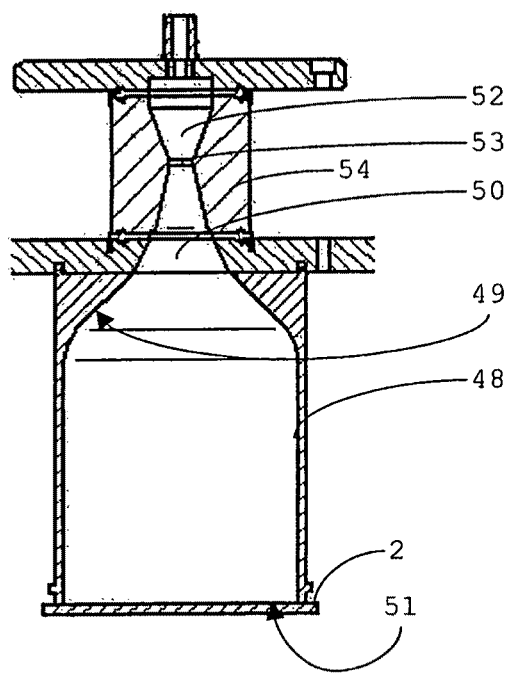
FIG. 19 is a schematic view of an assembly of the second embodiment of a dispersion chamber and a first embodiment of a replaceable module comprising a nozzle.

FIG. 19 illustrates an embodiment of an apparatus for dispersing a sample of particulate material wherein a nozzle 52 is provided at a position, in use, between the membrane of the sample-carrier (not shown in detail) and the inlet duct 50 attached to the second bell 48. The nozzle 52 is a convergent-divergent nozzle, used to achieve a condition of choked flow, so that the velocity of the volume of fluid dispersing the sample is determined by the geometry of the nozzle 52. Particles entrained by the fluid are accelerated to a relatively high velocity in a throat 53 of the nozzle 52, whereupon they slow down as they enter the dispersion chamber through the divergent inlet duct 50. This configuration is suitable for dispersing particulate material requiring a relatively high speed for separation. Nevertheless, the risk of particles breaking up on impact with the specimen plate 2 or with inner walls of the second bell 48 is kept relatively low. The particles decelerate on passing the throat 53.

It is noted that the nozzle 52 is included in a replaceable module 54, arranged to be mounted to the second bell 48 and to allow a fitting such as the fitting 13 to be connected to it. Thus, using this embodiment of the apparatus, a nozzle configuration can be chosen to suit the type of sample being dispersed. To this end, the assembly 1 for particle size analysis is provided with a set of replaceable modules, each including a nozzle of different dimensions and/or geometry. The module 54 is adapted to receive one of the modules 28,30,34 of the sample-carriers 29,33.

Figure 20:
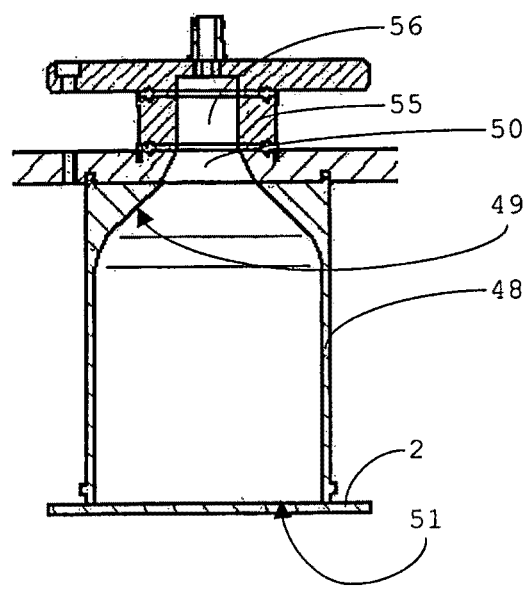
FIG. 20 is a schematic view of an assembly of the second embodiment of a dispersion chamber and a second embodiment of a replaceable module comprising a nozzle.

FIG. 20 shows the second bell 48 with a different replaceable module 55, comprising a differently configured nozzle 56, mounted to it. The nozzle 56 as illustrated in FIG. 20 is generally circle-cylindrical. It is suitable for dispersing fragile particles of a free-flowing nature.

Figure 21:
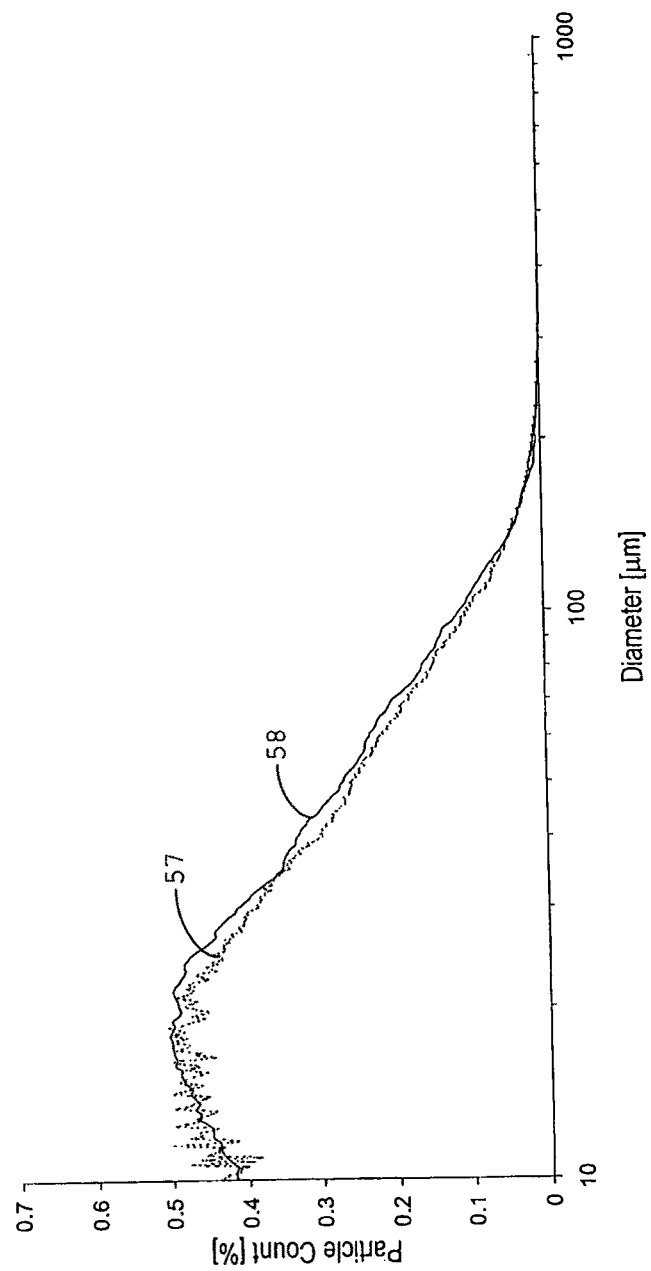
FIG. 21 is a diagram illustrating the results of a comparative test carried out between a prototype of the assembly of FIG. 1 and an apparatus for dispersing a sample of particles in oil.

Various features allowing adaptation of the apparatus for dispersing a sample of particulate material whilst retaining consistent repeatability of results have been described. FIG. 21 illustrates the results of a comparative test carried out using a sample of crystals of a salt of a pharmaceutically active compound. The crystals are known to have a needle-like shape with sizes in the range of 10 μm to 1000 μm. Such particles are liable to fracture in a dry powder dispersion method using excessive dispersion energy. A sure sign of this occurring is a loss of material in the larger portion of the size distribution. For comparison, a sample of the same powder was dispersed in an oil dispersion. The size measurement was carried out using the same set-up, except that a different objective (with a larger depth of field and lower magnification) was use to image the sample dispersed in oil. A smoothing operation was applied to obtain the two graphs illustrated in FIG. 21. A first graph 57 illustrates the size distribution in the sample dispersed in oil, whereas a second graph 58 illustrates the size distribution of the sample dispersed using a prototype of the assembly 1 for particle size analysis. Only the range from 10 µm is shown for clarity, since artifacts are obtained for lower values and the percentage fraction in the higher size classes is too small for a meaningful comparison. It can be seen that the apparatus for dispersing a sample of particulate material as described herein has the property of avoiding break-up of fragile particles.

Figure 22:
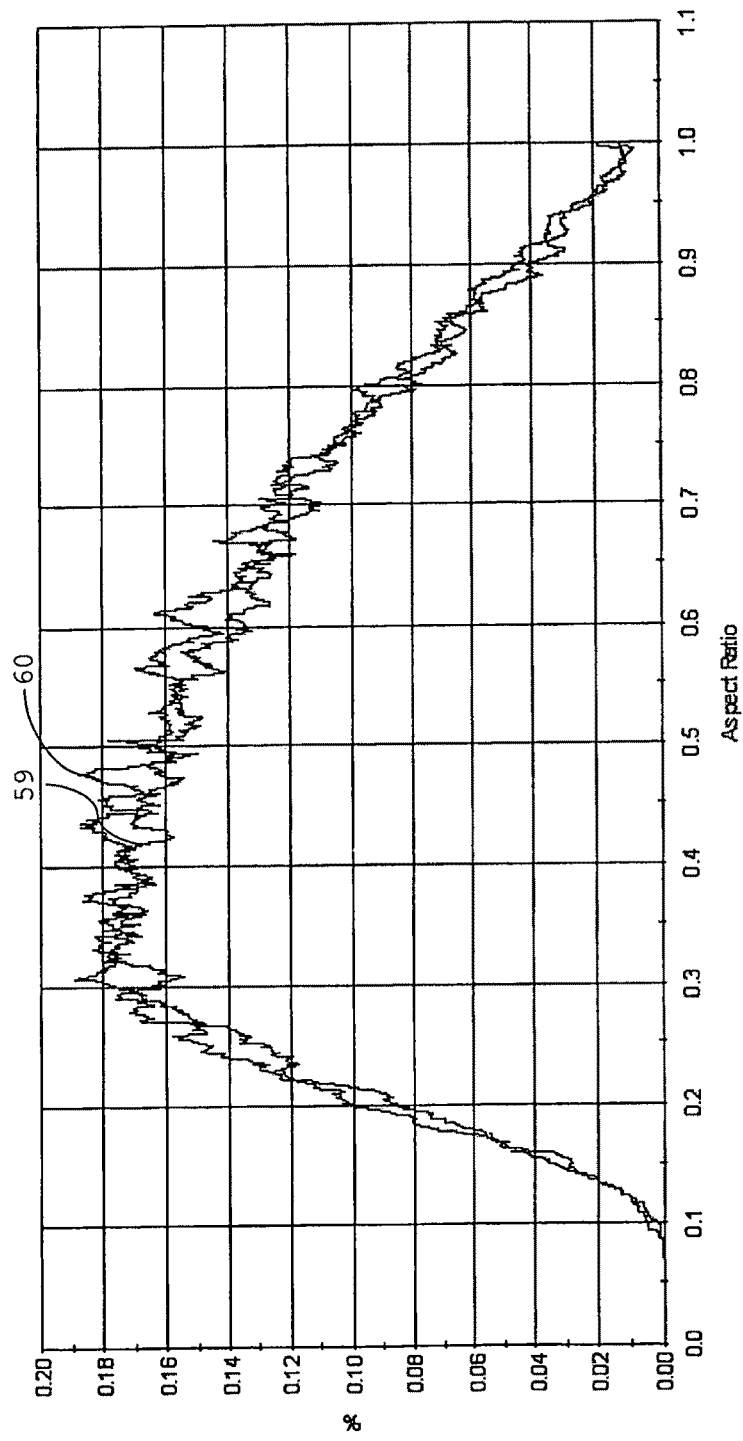
FIG. 22 is a diagram illustrating the results of a comparative test comparing the aspect ratio distribution of a sample dispersed using a prototype of the assembly of FIG. 1 and a sample dispersed by hand.

A useful quantitative measure of the quality of dispersion of a sample of elongated particles is provided by the particle aspect ratio. Aspect ratio distributions for a different comparative example, using a sample of the same particles as the example of FIG. 21, are illustrated in FIG. 22. A first graph 59 shows the aspect ratio distribution for a sample dispersed by hand to ensure that no particles overlap. This process, taking up to three hours, is far too laborious to be practical, but provides a perfect distribution as far as subsequent particle analysis is concerned. A second graph 60 shows the aspect ratio distribution for the sample dispersed using the prototype of the assembly 1.

The second graph 60 was obtained using a dispersion method employing a dual-disc sample carrier 33 including a membrane 35 arranged to rupture upon application of a sufficient pressure differential across the membrane 35, but not in any way weakened by scoring. Instead, the membrane 35 and upstream disc 36 each comprised a piece of aluminium foil, about 6.4 µm in thickness, more commonly used to manufacture capacitors. This embodiment could therefore be manufactured at a relatively low cost. For reproducible rupture the membrane was subjected to a pressure pulse with a pre-determined pressure profile and a pre-determined peak value. In this case, a progressive pressure ramp with increments of 0.1 bar was applied.

The main conclusion that can be drawn from the diagram shown in FIG. 22 is that the aspect ratio distribution is almost identical for the two techniques. The dispersion techniques outlined herein do not lead to a shift to aspect ratio values indicative of large-scale particle shattering.

The invention is not limited to the described embodiments, which can be varied within the scope of the claims. For example, A pulsed positive pressure differential can also be provided by pressurising both the dispersion chamber 15 and the fluid supply line in which the carrier having the sample-bearing surface is placed relative to ambient pressure, and subsequently bringing the dispersion chamber 17 to ambient pressure, e.g. by using suitable pressure release mechanisms.

The invention claimed is:

1. An assembly for particle analysis comprising:

I. an apparatus for dispersing a sample of particulate material for deposition on a sample collection surface, the apparatus including:

a) a carrier having a sample-bearing surface on which to place the sample, the carrier being arranged such that the sample-bearing surface is removed from contact with the sample upon application of a sufficient pressure differential across the carrier between the sample-bearing surface and an opposite side of the carrier, wherein the apparatus includes b) a fluid-filled housing for forming a dispersion chamber, at least when closed off at a base by the sample collection surface, the housing having an inlet at least partially facing the base, c) an apparatus for passing a volume of fluid past the carrier through the inlet by subjecting the carrier to a pulsed positive pressure differential relative to the dispersion chamber, and in that the housing is already filled with fluid, and d) a system for subjecting the carrier to a pressure pulse with a pre-determined pressure profile which is independent of the geometry of the inlet and housing, and II. an apparatus for analysis of particles of the sample of particulate material deposited on the sample collection surface.

2. The assembly according to claim 1, including a system for controlling the volume of fluid passed past the carrier independently of the volume of the housing.

3. The assembly according to claim 1, wherein the carrier includes a membrane arranged to rupture upon application of a sufficient pressure differential across the membrane.

4. The assembly of claim 3 comprising a set of membranes for use in the apparatus, wherein at least some of the membranes are arranged to rupture at different respective values of the pressure differential.

5. The assembly of claim 3 wherein the apparatus includes a fitting for receiving a module supporting the membrane in the path of flow of fluid conducted, in use, by a duct in fluid connection with the inlet, the fitting including a mechanism for engaging the module such as to hold the module in a pre-determined orientation, wherein the sample carrier includes the module supporting the membrane.

6. The assembly according to claim 5, further including an upstream disc, configured to rupture at a certain pressure differential across the disc, the sample carrier being suitable for placement in the path of flow in such an orientation that the disc is positioned upstream of the membrane.

7. The assembly according to claim 6, wherein the disc is configured to rupture at a higher pressure differential across the disc than that across the membrane at which the membrane is arranged to rupture.

8. The assembly according to claim 3, wherein the membrane is weakened according to a pattern, symmetric with respect to a normal to the sample-bearing surface.

9. The assembly according to claim 3, wherein the membrane is weakened along a plurality of line segments from the group:

(i) line segments extending in respective essentially radial direction with respect to a normal to the sample-bearing surface and (ii) at least three radially extending line segments and, to a lesser extent than along the radially extending line segments, along at least one line segment connecting points removed from radially innermost end points on angularly neighbouring ones of the radially extending line segments.

10. The assembly according to claim 3, including a fitting for receiving a module supporting the membrane in the path of flow of fluid conducted, in use, by a duct in fluid connection with the inlet, wherein the fitting includes a mechanism for engaging the module such as to hold the module in a pre-determined orientation.

11. The assembly according to claim 1, wherein the carrier is removably arranged in the apparatus.

12. The assembly according to claim 1, wherein at least the sample-bearing surface is electrically conducting, and wherein the sample-bearing surface is electrically connected to earth.

13. The assembly according to claim 1, wherein the apparatus for passing a volume of fluid past the carrier through the inlet is arranged to subject the carrier to a pulsed positive pressure differential relative to an ambient air pressure.

14. The assembly according to claim 1, wherein the housing comprises a bell, the apparatus further including a mechanism for positioning the sample collection surface in a position facing the base of the bell and a mechanism for causing relative movement between the sample collection surface and the bell so as to position the base against the sample collection surface, and wherein the assembly includes an x-y stage of an imaging system integrated with the apparatus.

15. The assembly according to claim 1, wherein a nozzle is provided at a position, in use, between the carrier and the inlet and wherein the nozzle is included in a replaceable module and the apparatus is arranged to allow mounting of the replaceable module.

16. The assembly according to claim 15, wherein the nozzle is one of:
a convergent-divergent nozzle; and
a cylindrical nozzle.

17. The assembly according to claim 1, including an upstream disc, configured to rupture at a certain pressure differential across the disc, wherein the apparatus is configured to allow placement of the disc in a position upstream of the carrier in a duct for supplying the volume of fluid.

18. The assembly according to claim 17, wherein the upstream disc is configured to rupture at a higher pressure differential than the pressure differential sufficient to remove the sample-bearing surface from contact with the sample.

19. The assembly according to claim 17, configured to accommodate a replaceable sample carrier comprising the carrier having the sample-bearing surface and the upstream disc, in the path of flow of fluid conducted, in use, by a duct in fluid connection with the inlet.

20. The assembly of claim 1
wherein the housing of the apparatus for dispersing a sample of particulate material comprises a bell, and
wherein the assembly further includes a mechanism for moving a collection means provided in the assembly between a position in which the sample collection surface faces the base of the bell and a position within a field of view of an imaging device.

21. The assembly according to claim 20, including a stage configured to support the collection means, wherein the sample collection surface is of sufficiently large dimensions as to cover the base of the bell to form the dispersion chamber, and wherein the mechanism is further arranged to position the collection means in a direction substantially normal to its sample collection surface.

22. Method of dispersing a sample of particulate material for particle analysis, the method including:
providing the sample on a sample-bearing surface of a carrier, the carrier being arranged such that the sample-bearing surface is removed from contact with the sample upon application of a sufficient pressure differential across the carrier between the sample-bearing surface and an opposite surface of the carrier,
providing a sample collection surface in a fluid-filled dispersion chamber, wherein the carrier with the sample is provided in the path of flow of fluid conducted, in use, by a fluid duct leading to the dispersion chamber,
passing a volume of fluid though the fluid duct by subjecting the carrier to a pulsed positive pressure differential relative to the dispersion chamber, and controlling the volume of fluid through the fluid duct to influence characteristics of a dispersing shear flow established upon removal of the sample-bearing surface from contact with the sample to thereby deposit particles of the sample on the sample collection surface, and
analysing the particles deposited on the sample collection surface.

23. Method according to claim 22, wherein the dispersion chamber contains a fluid to at least an amount equivalent to the amount of air at ambient air pressure at room temperature prior to the volume of fluid being passed through the fluid duct, and including tailoring at least part of a pressure pulse to which the carrier is subjected to conform to at least one of a pre-determined profile or peak value.

24. Apparatus for dispersing a sample of particulate material, including:
a carrier having a sample-bearing surface on which to place the sample,
the carrier being arranged such that the sample-bearing surface is removed from contact with the sample upon application of a sufficient pressure differential across the carrier between the sample-bearing surface and an opposite side of the carrier, wherein
the apparatus includes a fluid-filled housing for forming a dispersion chamber, at least when closed off at a base, the housing having an inlet at least partially facing the base, and the apparatus includes an apparatus for passing a volume of fluid past the carrier through the inlet by subjecting the carrier to a pulsed positive pressure differential relative to the dispersion chamber, and in that the housing is already filled with fluid, and wherein the apparatus also includes a system for subjecting the carrier to a pressure pulse with a pre-determined pressure profile which is independent of the geometry of the inlet and housing,
wherein the membrane is weakened according to a pattern, symmetric with respect to a normal to the sample-bearing surface.

25. The apparatus of claim 24 wherein the membrane is weakened along a plurality of line segments from the group:—(i) line segments extending in respective essentially radial direction with respect to a normal to the sample-bearing surface and (ii) at least three radially extending line segments and, to a lesser extent than along the radially extending line segments, along at least one line segment connecting points removed from radially innermost end points on angularly neighbouring ones of the radially extending line segments.

26. The apparatus of claim 24 including a fitting for receiving a module supporting the membrane in the path of flow of fluid conducted, in use, by a duct in fluid connection with the inlet, wherein the fitting includes a mechanism for engaging the module such as to hold the module in a pre-determined orientation.

27. Apparatus for dispersing a sample of particulate material, including:
a carrier having a sample-bearing surface on which to place the sample,
the carrier being arranged such that the sample-bearing surface is removed from contact with the sample upon application of a sufficient pressure differential across the carrier between the sample-bearing surface and an opposite side of the carrier, wherein
the apparatus includes a fluid-filled housing for forming a dispersion chamber, at least when closed off at a base, the housing having an inlet at least partially facing the base,
and the apparatus includes an apparatus for passing a volume of fluid past the carrier through the inlet by subjecting the carrier to a pulsed positive pressure differential relative to the dispersion chamber, and in that the housing is already filled with fluid, and wherein the apparatus also includes a system for subjecting the carrier to a pressure pulse with a pre-determined pressure profile which is independent of the geometry of the inlet and housing, wherein the carrier is removably arranged in the apparatus.

28. Apparatus for dispersing a sample of particulate material, including:

a carrier having a sample-bearing surface on which to place the sample, the carrier being arranged such that the sample-bearing surface is removed from contact with the sample upon application of a sufficient pressure differential across the carrier between the sample-bearing surface and an opposite side of the carrier, wherein the apparatus includes a fluid-filled housing for forming a dispersion chamber, at least when closed off at a base, the housing having an inlet at least partially facing the base, and the apparatus includes an apparatus for passing a volume of fluid past the carrier through the inlet by subjecting the carrier to a pulsed positive pressure differential relative to the dispersion chamber, and in that the housing is already filled with fluid, and wherein the apparatus also includes a system for subjecting the carrier to a pressure pulse with a pre-determined pressure profile which is independent of the geometry of the inlet and housing, wherein at least the sample-bearing surface is electrically conducting, and wherein the sample-bearing surface is electrically connected to earth.

29. Apparatus for dispersing a sample of particulate material, including:

a carrier having a sample-bearing surface on which to place the sample, the carrier being arranged such that the sample-bearing surface is removed from contact with the sample upon application of a sufficient pressure differential across the carrier between the sample-bearing surface and an opposite side of the carrier, wherein the apparatus includes a fluid-filled housing for forming a dispersion chamber, at least when closed off at a base, the housing having an inlet at least partially facing the base, and the apparatus includes an apparatus for passing a volume of fluid past the carrier through the inlet by subjecting the carrier to a pulsed positive pressure differential relative to the dispersion chamber, and in that the housing is already filled with fluid, and wherein the apparatus also includes a system for subjecting the carrier to a pressure pulse with a pre-determined pressure profile which is independent of the geometry of the inlet and housing, wherein a nozzle is provided at a position, in use, between the carrier and the inlet and wherein the nozzle is included in a replaceable module and the apparatus is arranged to allow mounting of the replaceable module.

30. The apparatus of claim 29 wherein the nozzle is one of:

a convergent-divergent nozzle; and a cylindrical nozzle.

31. Apparatus for dispersing a sample of particulate material, including:

a carrier having a sample-bearing surface on which to place the sample, the carrier being arranged such that the sample-bearing surface is removed from contact with the sample upon application of a sufficient pressure differential across the carrier between the sample-bearing surface and an opposite side of the carrier, wherein the apparatus includes a fluid-filled housing for forming a dispersion chamber, at least when closed off at a base, the housing having an inlet at least partially facing the base, and the apparatus includes an apparatus for passing a volume of fluid past the carrier through the inlet by subjecting the carrier to a pulsed positive pressure differential relative to the dispersion chamber, and in that the housing is already filled with fluid, and wherein the apparatus also includes a system for subjecting the carrier to a pressure pulse with a pre-determined pressure profile which is independent of the geometry of the inlet and housing, including an upstream disc, configured to rupture at a certain pressure differential across the disc, wherein the apparatus is configured to allow placement of the disc in a position upstream of the carrier in a duct for supplying the volume of fluid, wherein the upstream disc is configured to rupture at a higher pressure differential than the pressure differential sufficient to remove the sample-bearing surface from contact with the sample.

32. Apparatus for dispersing a sample of particulate material, including:

a carrier having a sample-bearing surface on which to place the sample, the carrier being arranged such that the sample-bearing surface is removed from contact with the sample upon application of a sufficient pressure differential across the carrier between the sample-bearing surface and an opposite side of the carrier, wherein the apparatus includes a fluid-filled housing for forming a dispersion chamber, at least when closed off at a base, the housing having an inlet at least partially facing the base, and the apparatus includes an apparatus for passing a volume of fluid past the carrier through the inlet by subjecting the carrier to a pulsed positive pressure differential relative to the dispersion chamber, and in that the housing is already filled with fluid, and wherein the apparatus also includes a system for subjecting the carrier to a pressure pulse with a pre-determined pressure profile which is independent of the geometry of the inlet and housing, including an upstream disc, configured to rupture at a certain pressure differential across the disc, wherein the apparatus is configured to allow placement of the disc in a position upstream of the carrier in a duct for supplying the volume of fluid, wherein the apparatus is configured to accommodate a replaceable sample carrier comprising the carrier having the sample-bearing surface and the upstream disc, in the path of flow of fluid conducted, in use, by a duct in fluid connection with the inlet.

* * * * *